United States Patent
Garton et al.

(10) Patent No.: US 7,081,554 B2
(45) Date of Patent: Jul. 25, 2006

(54) OXO PROCESS

(75) Inventors: Ronald D. Garton, Baton Rouge, LA (US); James T. Ritchie, Zachary, LA (US); Raphael Frans Caers, Edegem (BE)

(73) Assignee: ExxonMobil Chemical Patent Inc., Houston, TX (US)

( * ) Notice: Subject to any disclaimer, the term of this patent is extended or adjusted under 35 U.S.C. 154(b) by 0 days.

(21) Appl. No.: 10/509,191

(22) PCT Filed: Mar. 28, 2003

(86) PCT No.: PCT/US03/09734

§ 371 (c)(1),
(2), (4) Date: Sep. 23, 2004

(87) PCT Pub. No.: WO03/082789

PCT Pub. Date: Oct. 9, 2003

(65) Prior Publication Data

US 2005/0215828 A1    Sep. 29, 2005

Related U.S. Application Data

(60) Provisional application No. 60/368,926, filed on Mar. 29, 2002.

(51) Int. Cl.
*C07C 45/50* (2006.01)
(52) U.S. Cl. ............ 568/429; 568/444; 568/451; 568/454
(58) Field of Classification Search ............ 568/429, 568/444, 451, 454
See application file for complete search history.

(56) References Cited

U.S. PATENT DOCUMENTS

| | | | |
|---|---|---|---|
| 2,638,485 A | 5/1953 | Mertzweiller | 260/604 |
| 2,744,936 A | 5/1956 | Mertzweiller | 260/604 |
| 2,754,332 A | 7/1956 | Mason | 260/604 |
| 2,757,204 A | 7/1956 | Ratcliff | 260/604 |
| 2,757,205 A | 7/1956 | Mertzweiller et al. | 260/604 |
| 2,757,206 A | 7/1956 | Jones et al. | 260/604 |
| 2,767,217 A | 10/1956 | Moise et al. | 260/604 |
| 2,768,974 A | 10/1956 | Krebs et al. | 260/604 |
| 2,812,356 A | 11/1957 | Aldridge et al. | 260/604 |
| 2,816,933 A | 12/1957 | Mertzweiller | 260/638 |
| 2,834,815 A | 5/1958 | Mertzweiller et al. | 260/638 |
| 3,055,942 A | 9/1962 | Roming, Jr. | 260/604 |
| 3,960,978 A | 6/1976 | Givens et al. | 260/683.15 R |
| 4,021,502 A | 5/1977 | Plank et al. | 260/683.15 R |
| 4,076,842 A | 2/1978 | Plank et al. | 423/328 |
| 4,150,062 A | 4/1979 | Garwood et al. | 260/673 |
| 4,211,640 A | 7/1980 | Garwood et al. | 208/255 |
| 4,410,090 A | 10/1983 | Sindermann | |
| 4,520,221 A | 5/1985 | Hsia Chen | 585/517 |
| 4,522,929 A | 6/1985 | Chester et al. | 502/77 |
| 4,524,232 A | 6/1985 | Chester et al. | 585/517 |
| 4,547,613 A | 10/1985 | Garwood et al. | 585/533 |
| 4,568,786 A | 2/1986 | Hsia Chen et al. | 585/517 |
| 4,625,067 A | 11/1986 | Hanin | 568/451 |
| 4,855,527 A | 8/1989 | Page et al. | 585/527 |
| 4,870,038 A | 9/1989 | Page et al. | 502/62 |
| 5,026,933 A | 6/1991 | Blain et al. | 585/7 |
| 5,112,519 A | 5/1992 | Giacobbe et al. | 252/174.21 |
| 5,130,107 A | 7/1992 | De Munck et al. | 423/144 |
| 5,218,134 A | 6/1993 | Pruett et al. | 560/239 |
| 5,237,105 A | 8/1993 | Summerlin | 568/451 |
| 5,245,072 A | 9/1993 | Giacobbe et al. | 560/99 |
| 5,321,168 A | 6/1994 | Roussel et al. | 568/882 |
| 5,410,090 A | 4/1995 | Beadle et al. | 568/451 |
| 5,417,869 A | 5/1995 | Giacobbe et al. | 252/33.6 |
| 5,457,240 A | 10/1995 | Beadle et al. | 568/451 |
| 5,985,804 A | 11/1999 | Ashjian et al. | 508/287 |
| 6,013,851 A | 1/2000 | Verrelst et al. | 585/533 |
| 6,015,928 A | 1/2000 | Gubisch et al. | 568/882 |
| 6,150,322 A | 11/2000 | Wright et al. | 514/16 |
| 2001/0023306 A1 | 9/2001 | Kaizik et al. | 568/451 |

FOREIGN PATENT DOCUMENTS

DE    2056342    5/1972
EP    0 643 683    8/1997

OTHER PUBLICATIONS

Abstract, DE 2056342, "Nonanal by Oxo Synthesis", dated May 25, 1972.

*Primary Examiner*—Sikarl A. Witherspoon
(74) *Attorney, Agent, or Firm*—Andrew B. Griffis

(57) ABSTRACT

The Oxo Process that recycles its cobalt primarily as cobalt salt is improved by concentration of the cobalt salt solution from the demetalling section and the addition of a separation step for organic acid and water. This allows for a higher reuse of acid in the process and thus a lower amount of acid in the waste water. Injecting a higher concentration of cobalt salt solution to the reaction section also reduces the requirement for cobalt source.

10 Claims, No Drawings

US 7,081,554 B2

OXO PROCESS

CROSS REFERENCE TO RELATED APPLICATIONS

This application is a National Stage Application of International Application No. PCT/US03/09734, filed Mar. 28, 2003, which claims the benefit of Provisional Application No. 60/368,926, filed Mar. 29, 2002. These applications are hereby incorporated by reference.

FIELD OF THE INVENTION

The invention relates to the production of alcohols by hydroformylation processes using low molecular weight organic acids in the decobalting stage.

BACKGROUND

Hydroformylation reactions involve the preparation of oxygenated organic compounds by the reaction of synthesis gas (carbon monoxide and hydrogen) with carbon compounds containing olefinic unsaturation (hereinafter "olefinic material"). The reaction is generally performed in the presence of a hydroformylation catalyst such as cobalt or rhodium, and results in the formation of a product comprising an aldehyde which has one more carbon atom in its molecular structure than the starting olefinic feedstock. By way of example, higher alcohols useful as intermediates in the manufacture of plasticizers, detergents, solvents, synthetic lubricants, and the like, are produced commercially in the so-called Oxo Process (i.e., transition metal catalyzed hydroformylation) by conversion of $C_3$ or higher olefin fractions (typically $C_5$–$C_{12}$) to an aldehyde-containing oxonation product having one additional carbon atom (e.g., $C_6$–$C_{13}$). Hydrogenation and distillation yields the respective alcohols, or the aldehydes may instead be further oxidized to the respective acids.

The Oxo Process to convert olefinic material to aldehydes generally proceeds through three basic stages as explained below by specific reference to a catalyst comprising cobalt.

In the first stage, or oxonation reaction, the olefinic material and the proper proportions of CO and $H_2$ are reacted in the presence of a cobalt-containing carbonylation catalyst to give a product comprising predominantly aldehydes containing one more carbon atom than the reacted olefin. Typically, alcohols, paraffins, acetals, and other species are also produced in the hydroformylation reaction. The catalyst can be supplied to this section by numerous methods known in the art, such as by injecting cobalt acetate or cobalt formate directly or by supplying cobalt from a precarbonylation stage or catalyst makeup stage in the form of a cobalt anion ($Co^{-1}$) or organically soluble form of $Co^{+2}$, such as cobalt naphthalate, oleate, or cobalt oxides.

The oxygenated organic mixture from the oxonation (or oxo) reactor(s), which typically contains various salts and molecular complexes of the metal from the catalyst (i.e., the "metal values") as well as the aldehydes, alcohols, acetals and other species, referred to as the crude aldehyde or crude hydroformylation mixture, is treated in a second stage, the demetalling stage. In the demetalling stage, typically a reaction is caused to separate the metal values from the aldehyde, such as by injecting dilute acetic and/or formic acid. This separation of the metal values is optionally helped by the additional injection of an oxidant. Various oxidants can be used including, but not limited to, oxygen, air or hydrogen peroxide, and can be used pure or diluted with inert diluents or inert carriers. The crude hydroformylation mixture separates into phases with the organic phase comprising the desired aldehyde separated from the aqueous phase comprising the cobalt as a salt exemplified by cobalt acetate and/or formate. The organic phase is sent to other unit operations downstream to be converted to the desired final product.

In the third stage of the Oxo Process the metal values removed in the second stage are worked up in a way that they can be reused in the oxonation section. There are several ways taught in the prior art to work up this catalyst. For example, one way is to convert the aqueous metal salt to an organically miscible compound such as cobalt naphthenate, and inject it directly into the oxonation reactor(s). Another way is to subject the aqueous salt solution in the presence of an organic solvent to high pressure synthesis gas, converting it to active carbonyl, and delivering it to the oxonation section via extraction, stripping or the like. It would be ideal if all of the cobalt is recovered and eventually passed in the proper form to the first stage described above.

These aforementioned three process stages may occur in more or less than three distinct vessels and numerous variations and improvements, including adding to, deleting from, or combining these stages, have been proposed over the years with various degrees of success. Although the use of dilute low molecular weight organic acid to retrieve the cobalt values as its corresponding cobalt salt has been known for many years, efficient recycling of cobalt salt in the Oxo Process has heretofore proved to be elusive.

U.S. Pat. No. 2,816,933 observes that the most direct method of utilization of cobalt acetate consists of recycling directly the aqueous cobalt stream from the demetalling stage to the primary aldehyde synthesis zone of the oxonation reaction stage. The problem with such a scheme is it introduces considerable quantities of water in to the reactor. Excess water substantially decreases the olefin conversion and may result in reactor flooding and complete loss of reaction. Instead, the patent teaches that after injection of sufficient acetic acid to combine with all the cobalt present in the demetalling stage, the entire mixture, including crude product, is allowed to separate into aldehyde and aqueous phases in a settler. After sufficient time, the lower aqueous phase containing cobalt acetate is passed to an extraction vessel where the cobalt salt is converted into oil soluble form and finally after numerous additional steps is used to supply a portion of the catalyst requirements for the oxonation reaction. Such a procedure is complex and inefficient and adds to the operating cost of the process. In addition acetic acid is highly soluble in the organic phase and without additional treatment too much acetic acid passes with the crude aldehyde to the hydrogenation (or hydro) stage. Such "additional treatment", for instance washing with fresh water, is economically and environmentally unattractive.

Numerous other variations on the Oxo Process are taught, for instance, in U.S. Pat. Nos. 2,638,485; 2,744,936; 2,754,332; 2,757,204; 2,757,206; 2,768,974; 2,812,356; and 3,055,942.

It has been recognized that many forms of cobalt catalyze the oxonation reaction. One preferred method of supplying the catalyst is to employ the oil-soluble $Co^{+2}$ compounds, such as cobalt naphthenate. After the carbonylation reaction and decobalting of the crude product in the demetalling stage, a catalyst makeup stage is required to convert the $Co^{+2}$ back to the oil-soluble form. In an attempt to avoid this catalyst makeup stage, U.S. Pat. No. 2,834,815 teaches the use of solid cobalt acetate, preferably added as a slurry with the olefin feed. Water or dilute acetic acid is then used to decobalt the crude aldehyde product and solid cobalt acetate is recovered by evaporation of the aqueous acetate solution. This process, however, provides for low olefin conversion when compared with the use of the oil-soluble cobalt catalysts and is difficult to run such a process, with recycling, in a continuous manner.

In another effort to avoid the catalyst makeup stage but taking what might be considered the opposite approach, U.S. Pat. No. 2,757,205 teaches that under appropriate conditions of temperature and pressure the use of $H_2$ and CO in the demetalling step produces a cobalt carbonyl ($Co^{-1}$) species that may be recycled to the oxonation reactor. The demetalling step still utilizes the addition of aqueous acetic acid, however the cobalt may be concentrated by distilling off the acid and water. The patent explicitly states that such a concentration step is not possible with cobalt acetate or formate (see col. 4, line 27+, of the patent). U.S. Pat. No. 2,767,217 teaches a variation of this process.

U.S. Pat. No. 4,625,067 describes recovery of cobalt values by contacting the hydroformylation crude product with a stripping gas to entrain more than 60% of the cobalt values as volatile cobalt compounds, in the presence of water or aqueous acid ("Cobalt Flash Process"). After contacting the crude product with the stripping gas (preferably synthesis gas), the cobalt-containing aqueous phase is separated and concentrated in a concentrator, preferably by flashing the aqueous phase in an evaporator. This aqueous phase then only contains a portion of the cobalt values in the hydroformylation product, because more than 60%, typically 70%, and preferentially as much as 80% of the cobalt is entrained with the stripping gas as volatile cobalt. This process preferably uses cobalt formate/formic acid solutions. In practice it has been found that acetic acid is not advantageously used in this process for several reasons, not the least of which being that since acetic acid is so soluble in the organic phase, too much is lost to the system with the extraction of the product in the demetalling stage. U.S. Pat. Nos. 4,410,090, 5,218,134 and 5,237,105 describe further improvements of the Cobalt Flash Process, all of them comprising as an essential step in the cobalt recycle process to hydroformylation a step wherein the cobalt is transferred using a vapor stream carrier like a stripping gas.

Finally, U.S. Pat. No. 6,015,928 teaches a process that combines a precarbonylation stage, where the catalyst is worked up in a form to be supplied to the reactor(s), and the oxonation reaction into a single two-phase reactor, where the $Co^{2+}$ salt is converted into $Co^{-1}$ compounds and taken up into the olefin phase.

Loss of dissolved cobalt salts and acid from the demetalling and cobalt workup stages continues to be a problem. Lack of efficient recycling techniques require that some portion of cobalt salt and acid is lost to the system and instead adds to the environmental load of the process. In a typical industrial process, cobalt losses via waste water are significant; see, for instance, U.S. Pat. No. 5,130,107.

Thus a more efficient means of recycling cobalt values, acid, and water is clearly desirable.

SUMMARY OF THE INVENTION

The present invention relates to a modification of the Oxo Process that includes a demetalling step wherein essentially all the cobalt values in the hydroformylation product are recovered as a water soluble cobalt salt including, but not limited to, formate and/or acetate, and which does not include a step in the cobalt recycle process wherein cobalt is transferred using a vapor stream carrier like a stripping gas.

The modification comprises the addition of a stage wherein the cobalt salt solution from the demetalling stage is concentrated and, optionally, a stage wherein the aqueous acid evaporated from the aforementioned concentration stage is separated from water, wherein the acid and water are optionally recycled, separately, into the modified Oxo Process according to the present invention. In a preferred embodiment, the acid is recycled to be injected into the demetalling stage. In another preferred embodiment, the water is used to wash the crude aldehyde product from the demetalling stage.

Thus, a principal object of the invention is to effect improved recycling of the cobalt values, and optionally water and acid, to reduce chemical consumption. A further object of the invention is to achieve higher throughput of olefin to aldehyde to increase capacity while lowering cost. Still a further object of the invention is to achieve lower emissions of acid and cobalt and lower water treatment required prior to discharge as waste in order to improve the environment.

These and other object, features, and advantages of the present invention will become apparent as reference is made to the following detailed description, preferred embodiments, specific examples and appended claims.

DETAILED DESCRIPTION

The present invention is an improvement on the Oxo Process to allow efficient recycle of cobalt values, acid and water.

The "Oxo Process" as used herein comprises: (1) a precarbonylation or catalyst makeup stage wherein the cobalt catalyst is formed and/or is supplied in the form of a cobalt anion (or $Co^{-1}$) or an organically soluble salt of $Co^{+2}$; (2) an oxonation (or carbonylation or hydroformylation) stage wherein an olefinic material is carbonylated in the presence of a cobalt catalyst; and (3) a demetalling stage where the majority of the cobalt in the hydroformylation product is recovered in the form of cobalt ($Co^{+2}$) salt, exemplified by cobalt acetate and/or formate. The Oxo Process as used herein excludes those processes in which at one stage in the cobalt recycle to the hydroformylation reaction the cobalt is transferred in its volatile form, using a vapor carrier like a stripping gas.

According to the present invention, there is added to the Oxo Process: (4) a stage wherein the aqueous solution from the demetalling stage comprising cobalt salt, a low molecular weight organic acid like acetic acid and/or formic acid, and water is concentrated in an evaporator; optionally (5) a stage wherein the acid and water evaporated from the aforementioned aqueous solution are separated into a concentrated acid phase and an acid-depleted water phase; and optionally (6) a stage wherein the crude aldehyde product from the demetalling stage is washed with the water from stage (5).

The first stage of the process is the precarbonylation or catalyst makeup stage, wherein an oil-soluble cobalt is supplied in the form of cobalt naphthenate, cobalt oleate, and the like, a step which is per se known in the art. In an alternative, or in addition to supplying the oil-soluble $Co^{+2}$, cobalt acetate ($Co^{+2}$) or cobalt formate is added. In a preferred embodiment of the present invention, at least a portion of the cobalt acetate or formate supplied in this stage is from the concentrator or evaporation stage which forms a principal part of the present invention, as described in detail below. When supplied as cobalt acetate or formate, the oil-soluble $Co^{-1}$ preforms in this stage in the presence of napthenate or oleate or other oil soluble anion, and/or the active catalyst may form in the next stage, or oxonation stage.

In a preferred embodiment of the present invention, the first stage and the second stage are combined and can occur in a single reactor having two phases, such as described in the aforementioned U.S. Pat. No. 6,015,928.

In the second stage, where the oil-soluble cobalt is mixed with the compound containing olefinic unsaturation (or olefinic material; e.g., an olefin) and synthesis gas, the carbonylation reaction occurs. One or more reactors are used and they are typically arranged in series. These reactors are referred to herein as the "oxonation reactor(s)" or "oxo reactor(s)". As is known in the art, the olefinic material and synthesis gas are typically added together into the oxo reactor(s) where they are mixed with the oil-soluble cobalt, or the olefinic material and synthesis gas are mixed with the oil-soluble cobalt prior to entering the oxo reactors. Many modifications of the foregoing are known.

The olefinic material used in step (2), above, may be short or long chained compounds containing olefinic unsaturation, depending on the final product desired. Most organic compounds possessing at least one non-aromatic carbon—carbon double bond may be reacted by this method. Generally the compound will have at least three carbon atoms although hydroformylation using ethylene is known (see, for instance, U.S. Pat. No. 6,150,322). Thus, straight and branched-chained olefins and diolefins such as propylene, butylenes, pentenes, hexenes, heptenes, butadiene, pentadiene, styrene, olefin polymers such as di- and tri-isobutylene and hexene and heptene dimers, olefinic fractions from the hydrocarbon synthesis process, thermal or catalytic cracking operations, and other sources of hydrocarbon fractions containing olefins may be used as starting material, depending upon the nature of the final product desired.

In a preferred embodiment, the olefinic material is a mixture of olefins having a carbon number of from $C_3$ to $C_{18}$, more preferably $C_5$ to $C_{18}$. It will be recognized that the olefin feed may not consist of 100% olefins within the specified carbon number range, but may be a distribution of mono-olefins having different carbon lengths with at least 50 wt. %, preferably 70 wt. %, more prefereably 80 wt. %, still more preferably 90 wt. % of mono-olefins in the specified carbon number range.

In another preferred embodiment, the olefinic material is the olefinic reaction product of the acid catalyzed oligomerization of propylene and/or butenes, which may also optionally include pentenes.

In yet another preferred embodiment, the olefinic material is the olefinic reaction product of the oligomerization of various olefins and compounds having olefinic unsaturation, using surface deactivated zeolite catalysts as described in U.S. Pat. Nos. 3,960,978; 4,021,502; 4,076,842; 4,150,062; 4,211,640; 4,520,221; 4,522,929; 4,524,232; 4,547,613; 4,568,786; 4,855,527; 4,870,038; 5,026,933; 5,112,519; 5,245,072; 5,417,869; 5,985,804; and 6,013,851.

Even more preferred as olefinic material in the present invention are $C_6$ to $C_{26}$ olefins, even more preferably $C_9$ to $C_{26}$ olefins, still more preferably $C_9$ to $C_{23}$ olefins, yet still more preferably $C_9$ to $C_{18}$ olefins, prepared by contacting lower olefins under polymerization conditions with siliceous monodimensional acidic zeolites such as ZSM-22 and ZSM-23 zeolite having pore activity and wherein the zeolite surface is rendered substantially inactive for acidic reactions. By "lower olefins" or "lower olefinic material" as used herein is simply meant that the starting material to be oligomerized over the zeolite have less carbon numbers than the final product. The oligomers may be dimers, trimers, tetramers or higher oligomers, or mixtures thereof. It is preferred that the starting material is a $C_3$ or greater olefin (or mixtures thereof), and in a preferred embodiment the olefinic material supplied to the oxonation reactor(s) according to the present invention derive from the oligomerization of $C_3$ and/or $C_4$ olefins using the aforementioned modified zeolites. In a particularly preferred embodiment, a feed is used comprising butenes (still more preferably n-butene) and propylene in the ratio of about 1:0.01 to 1:0.049 wt. %, yet still more preferably along with paraffins to act as a heat sink in the reaction. The amount of paraffins to use can be determined by one of ordinary skill in the art.

Yet still another preferred embodiment is the use of LAOs and/or LIOs (linear alpha olefins and linear internal olefins, respectively), which terms are well-known in the art, as olefinic feed.

Other more preferred olefinic materials used as a feed into the oxonation reactors include oligomers produced by the Octol® process or the Dimersol® process. See, for instance, the previously mentioned U.S. Pat. No. 6,015,928. Yet another more preferred olefinic material includes oligomers produced using solid phosphoric acid (SPA) catalysts and those produced using ZSM-57 catalysts, procedures which are known in the art.

Yet another more preferred feed comprises 0.1–20 wt. %, more preferably 0.5–5.0 wt. % isoolefin, particularly isobutylene and or isoamylene. A preferred source of such a feed is the unreacted effluent from an MTBE unit Reactor conditions for each stage are well-known in the art and are not critical to achieve the objects of the present invention. Typical hydroformylation reaction conditions include a temperature of about 90° C. to about 200° C., a pressure of about 2 MPa to about 30 MPa, and a catalyst to olefin ration of about 1:5000 to about 1:1. The molar ratio of hydrogen to carbon monoxide is usually about 0.5 to about 10, preferably from about 1.0 to about 2.0. The process may also be carried out in the presence of an inert solvent such as ketones, e.g, acetone, or aromatic compounds such as benzene, toluene and the xylenes.

In a preferred embodiment according to the present invention, the Oxo Process is modified so that the first and second stages described above are combined, such as set forth in the aforementioned U.S. Pat. No. 6,015,928. Thus, in a single stage there is combined the synthesis gas, the olefinic starting material, a cobalt catalyst in an organic phase, and an aqueous cobalt salt solution, and the oxonation reaction proceeds in this stage. In a preferred embodiment according to the present invention, the concentrated cobalt salt from the evaporator is used to supply this stage. The process according to the present invention then proceeds from the oxonation reactor(s) as further described below.

The product from the oxo reactor(s) is passed to the demetalling stage. According to the present invention, in this stage the cobalt values are separated from the desired aldehyde reaction product by injecting a dilute low molecular weight organic acid, exemplified by dilute acetic acid and/or formic acid, and optionally accompanied by the injection of an oxidant including, but not limited to, oxygen, hydrogen peroxide or air. The oxidant can be injected in a pure form or with an inert diluent. This step is preferably performed without addition of CO or $H_2$, so that cobalt salts, not cobalt carbonyl, especially not the volatile hydrido cobalt tetracarbonyl, or some other species, is the predominant form of the cobalt value recovered. In one embodiment according to the present invention, the cobalt values are recovered at least 70%, preferrably at least 80%, more preferrably at least 90%, and even more perferably at least 99% in the form of a cobalt salt. Proportions of ingredients, flow rates, and the like, are known in the art and are not the subject of the present invention. The crude aldehyde product in an organic phase is then processed to give the corresponding alcohol or acid by known processes, for example by hydrogenation and subsequent distillation. In a preferred embodiment the crude aldehyde product is passed to a wash tower where it is washed with water separated from the evaporator step which is described in more detail below. In another preferred embodiment of the invention the concentrated acid solution is added to the demetalling stage.

The aqueous phase from the demetalling reactor(s), containing cobalt values, acetic or formic acid, and water, is then processed by passing to an evaporator, which forms a principal aspect of the present invention. It is however possible, and even advantageous, to return part of the aqueous phase from the demetalling reactor(s) directly to the inlet of the demetalling stage. In that case only part of the aqueous phase from the demetalling reactor(s) is processed in the evaporator.

In the evaporator stage, the solution containing the cobalt values, principally in the form of cobalt salt, acetic and/or formic acid and water, is heated, preferably at atmospheric pressure, until a mixture of acid and water can be removed as distillate. Concentrated aqueous cobalt salt is taken off as bottoms from the reactor. More than one evaporator may be used and the evaporator units may be arranged in series or parallel. The evaporators may operate continuously or as batch units. The concentration of the cobalt salt in these units may be optionally monitored by means per se known in the art, such as by spectroscopic techniques, electrochemically, or by simple material balance control of the operation.

In a process according to the present invention the concentrated cobalt salt solution is passed directly either to the catalyst makeup stage or to the oxo reactor(s), or a combination thereof. The passing of the concentrated cobalt salt solution may be done in a batch fashion or continuously, but in either event it is important that the solution be metered carefully, as is well-known in the art, so that the appropriate proportion of cobalt salt and water species are added.

The acid and water distillate from the evaporator may be used in any known manner, such as treated as waste material, but in a preferred embodiment of the present invention the distillate is passed to a separator, where water and acid are separated into a concentrated acid stream and an acid-depleted stream or water. This may be accomplished in several ways, such as by distillation, membrane separation or solvent extraction (such as with ethyl acetate). Methods of separating aqueous acetic or formic acid into two streams, one rich in acid and one depleted in acid, are known.

For acetic acid, it is preferred that membrane separation be used in this step, more preferably reverse osmosis membrane separation. It is still more preferable that a polymeric membrane is used, the most preferred membrane being a membrane comprising an aromatic polyamide. Such systems are commercially available, for instance, from Osmonics, Inc., of Minnetonka, Minn., USA.

In another preferred embodiment, a pervaporation system such as that produced by Sulzer Chemtech GmbH Membrane Systems, Neunkirchen, Germany, can be used. The membrane material here is preferably polymeric or even more preferably ceramic.

In a still more preferred embodiment at least a portion of the concentrated acid stream separated from the acid-depleted stream in the aforementioned separation step is used in the demetalling stage. In another still more preferred embodiment, as mentioned above, at least a portion of the acid-depleted stream is used, alone or in combination with fresh water, in a wash tower to extract impurities from the crude decobalted aldehyde stream from the demetalling stage. In particular the "impurities" that are intended to be extracted include principally the acid itself, especially acetic acid, which is highly soluble in the organic phase separated out in the demetalling step. In yet another preferred embodiment, after the acid-depleted stream is used to extract acid from the organic phase in the aldehyde wash tower, at least a portion of the aqueous stream from the wash tower may be recycled back into the Oxo Process, such as by using at least a portion in the demetalling step, and/or by passing at least a portion of this stream through the acid/water separation step.

EXAMPLES

The following example is meant to illustrate the present invention. Numerous modifications and variations are possible and it is to be understood that within the scope of the appended claims, the invention may be practiced otherwise than as specifically described herein.

A olefin mixture comprising n-butene and propylene in a molar ratio of about 1:0.49 is oligomerized over a siliceous acidic ZSM-23 catalyst having acidic pore activity and surface neutralized with 2,4,6-collidine to produce a substantially linear $C_{10+}$ olefin mixture having methyl branching in accordance with the catalyst treatment and oligomerization procedures set forth in Example VII of U.S. Pat. No. 4,855,527.

The olefin mixture thus produced is introduced into the oxonation reactor in a process according to the present invention by mixing first with a stream from the catalyst makeup stage comprising cobalt naphthenate. The olefinic feed stream containing the oil-soluble cobalt is allowed in four reactors in series, in the presence of $H_2$ and CO under a pressure of 220 atmospheres for one hour and the crude product of this reaction is feed to the demetalling stage. Two stoichiometric proportions of acetic acid (relative to the amount of cobalt introduced to the oxonation reactors) and air are injected into the oxonation product. After mixing, the stream is allowed to separate into three phases in the demetalling vessel. The upper gas phase is discharged. The organic phase contains the crude oxo aldehyde that is processed further by passing to a wash tower, as detailed below. The lower (or bottoms) aqueous phase contains water, acetic acid and cobalt acetate.

The aldehyde portion taken from the demetalling reactor is passed to a wash tower where it is washed by a mixture of fresh water and the acetic acid-depleted water that has been recovered from the demetalling stage and separated, according to the present invention, by separating the distillate from the evaporator into a concentrated acetic acid portion and a acetic acid-depleted water portion, as described in more detail below. The thus-washed aldehyde is then further processed downstream, according to known procedures, to yield the corresponding alcohol.

The aqueous solution comprising acetic acid, water, and cobalt acetate, is passed to the evaporator operating at conditions sufficient to continually cause an acetic acid/water mixture to distill overhead.

The concentrated cobalt acetate portion that is taken as the bottom fraction from the evaporator is then split into three streams, each of which is metered, separately and independently, into the cobalt naphthenate stage reactor, and the first and second oxonation reactors, in such a manner that the cobalt concentration in the respective solutions is maximized.

The overhead distillate from the evaporator is passed through a reverse osmosis system including a polymeric membrane comprising an aromatic polyamide. A commercially available system from Osmonics, Inc, is used. In this case the overheads from the evaporator comprised 5.5 wt. % acetic acid. This stream is separated into a concentrated acetic acid stream and an acetic acid-depleted water stream in a 2-pass reverse osmosis system. The first pass comprises of 5 housings, arranged so that the stream is first passed through 2 parallel housings and then combined and passed through three housings in series (i.e., a 2-1-1-1 array). Each of the housings contain 6 Model AD4040 elements supplied by Osmonics, Inc., for a total of 30 elements. The first pass is operated at 1200 psig and 25° C. A small balance tank is placed between the first and second pass. The second pass comprises 2 housings in series, each containing 6 Model AD4040 elements, totaling 12 elements. The second pass is operated at 900 psig and 25° C. This system produces a 0.3 wt % acetic acid-depleted water stream (or "permeate" stream) at 7.2 gallon per minute (gpm) and a 2.8 gpm acetic acid concentrate stream with 18 wt % acetic acid.

The permeate stream is then used to wash the crude aldehyde from the demetalling stage in a 5-stage wash tower. A portion of the concentrate stream is recycled to the demetalling stage and a portion is recycled back to the first two oxonation reactors.

The above modified Oxo Process, operated in accordance with a most preferred embodiment of the present invention, results in a decrease of about 70% in the amount of fresh acetic acid that needs to be used when compared with the base Oxo Process not using the evaporator step.

It is to be noted that the same Oxo Process operating by recycling cobalt acetate without the evaporator experiences reactor flooding on a regular basis. Moreover it is to be noted that the aldehyde product washed with the permeate stream yields a commercially viable product on hydrogenation, whereas the same wash using the distillate stream from the evaporator without the membrane separation step actually has more acetic acid in it than before the wash and is not commercially saleable without expensive purification.

The present invention clearly solves several problems with the prior art Oxo Process, including but not limited to: (1) allowing for direct recycle of cobalt acetate into the oxonation reactor(s) with less ocurrance of reactor flooding, at least because the present invention provides for a more concentrated cobalt acetate stream (by the evaporator step); (2) decreasing the amount of fresh acetic acid that must be added to the system; and (3) decreasing the amount of fresh water necessary to wash the aldehyde product; the latter two problems solved at least because the present invention provides for the use of internal process fluids (from the combination of evaporator and separation steps).

As previously mentioned, the aldehyde product typically is processed downstream, such as by hydrogenation and distillation to alcohol or by further oxidation to acid. These products may also be further processed to more valuable species. For instance, it is particularly beneficial to esterify the alcohols produced according to the present invention for synthetic lubricant and plasticizer end uses. Alcohol ethoxylates from alcohols made according to the present invention, as well as the sulfonated alcohols, are valuable in the surfactant market, particularly in detergents.

Furthermore, the following preferred embodiments are identified, without any intent to limit the inventive concept nor the spirit of the appended claims by such preferred embodiments:

the hydroformylation of compounds having olefinic unsaturation using synthesis gas in the presence of a cobalt catalyst, including a demetalling step wherein substantially all of the cobalt is recovered as cobalt acetate and/or formate, the improvement comprising concentrating an aqueous stream comprising cobalt acetate and/or formate from the demetalling step in an evaporator under conditions sufficient to cause a stream of distillate comprising acetic and/or formic acid and water to distill overhead from the evaporator and withdrawing, as bottoms from the evaporator, a concentrated cobalt salt solution; and also a process for preparing an aldehyde comprising the following steps:

providing cobalt to form an oil-soluble cobalt carbonylation catalyst;

reacting synthesis gas and an olefinic material in the presence of said cobalt carbonylation catalyst under hydroformylation conditions to produce a mixture comprising an aldehyde;

injecting aqueous acetic and/or formic acid into said mixture, optionally together with an oxidant, to make an organic phase comprising said aldehyde and an aqueous phase comprising greater than 70%, preferably more than 80%, more preferably more than 90% of the cobalt as an organic salt like cobalt acetate and/or formate;

passing said aqueous phase to an evaporator wherein a distillate fraction comprising acid and water is taken overhead and a bottoms fraction comprising concentrated cobalt salt is removed from the evaporator;

recycling said cobalt salt to supply said cobalt in step (a); and recovering said aldehyde.

Even more preferred embodiments include modifying the above by: providing a stage after said concentration stage, wherein said distillate is separated into an acid-depleted stream and a concentrated acid stream; moreover, wherein said distillate is separated into an acetic acid-depleted stream and a concentrated acetic acid stream by reverse osmosis using a polymeric membrane; and further wherein an organic phase comprising an aldehyde is separated from an aqueous phase comprising cobalt salt in said demetalling step and passed to a wash tower, where it is washed with at least a portion of said acid-depleted stream; and further wherein the process comprises a precarbonylation or catalyst makeup stage and an oxonation stage, and wherein at least a portion of said concentrated cobalt salt from said evaporator is recycled back into at least one of said precarbonylation or catalyst makeup stage and said oxonation stage; and further wherein the olefinic material that is hydroformylated is made by oligomerizing a lower olefinic material over a siliceous acidic monodimensional zeolite selected from ZSM-22 and ZSM-23 having acidic pore activity and surface neutralized with a sterically hindered amine such as 2,4,6-collidine; and further wherein the olefinic material that is hydroformylated is made by a process selected from the Octol® process, the Dimersol® process, or using a solid phosphoric acid catalyst; and further wherein the concentrated acid stream is recycled to be used in the demetalling stage; and further wherein said precarbonylation stage and said oxonation stages are combined so that the hydroformylation reaction occurs in a single vessel comprising two phases, one phase comprising cobalt salt and the other phase comprising an oil-soluble cobalt form.

It should be noted that all patents cited herein are expressly incorporated herein by reference for all disclosures that are relevant to the present invention.

What is claimed is:

1. A process for the hydroformylation of compounds having olefinic unsaturation using synthesis gas in the presence of a cobalt catalyst, including a demetalling step wherein essentially all the cobalt from the hydroformylation reaction is recovered as cobalt acetate and/or cobalt formate and the cobalt recycle process to hydroformylation does not include a step where the cobalt is transferred using a vapor stream carrier, the improvement comprising concentrating an aqueous stream comprising cobalt acetate and/or formate from the demetalling step in an evaporator under conditions sufficient to cause a stream of distillate comprising acetic and/or formic acid and water to distill overhead from the evaporator and withdrawing, as bottoms from the evaporator, a concentrated cobalt acetate and/or cobalt formate solution.

2. The process according to claim 1, wherein the stream of distillate comprises acetic acid and water and the bottoms from the evaporator comprises a concentrated cobalt acetate solution.

3. The process according to claim 1, further comprising a stage after said concentration stage, wherein said distillate is separated into an acid-depleted stream and a concentrated acid stream.

4. The process according to claim 3, wherein said distillate is separated into an acid-depleted stream and a concentrated acid stream by reverse osmosis using a polymeric membrane.

5. The process according to claim 3, wherein an organic phase comprising an aldehyde is separated from an aqueous phase comprising cobalt salt in said demetalling step and passed to a wash tower, where it is washed with at least a portion of said acid-depleted stream.

6. The process according to claim 1, further comprising a precarbonylation or catalyst makeup stage and an oxonation stage, and wherein at least a portion of said concentrated cobalt salt from said evaporator is recycled back into at least one of said precarbonylation or catalyst makeup stage and said oxonation stage.

7. The process according to claim 1, wherein the olefinic material that is hydroformylated is made by oligomerizing a lower olefinic material over a siliceous acidic monodimensional zeolite selected from ZSM-22 and ZSM-23 having acidic pore activity and surface neutralized with 2,4,6-collidine.

8. The process according to claim 3, wherein the concentrated acid stream is recycled to be used in the demetalling stage.

9. The process according to claim 6, wherein said precarbonylation stage and said oxonation stages are combined so that the hydroformylation reaction occurs in a single vessel comprising two phases, one phase comprising cobalt salt and the other phase comprising an oil-soluble cobalt form.

10. A process comprising the following steps:
(a) providing in a single vessel cobalt acetate and/or formate, and an oil-soluble cobalt carbonylation catalyst;
(b) reacting synthesis gas and olefinic material in the presence of said cobalt carbonylation catalyst under hydroformylation conditions to produce a mixture comprising an aldehyde;
(c) injecting aqueous acetic and/or formic acid into said mixture to make an organic phase comprising said aldehyde and an aqueous phase comprising cobalt acetate and/or formate;
(d) passing said aqueous phase to an evaporator wherein a distillate fraction comprising acetic and/or formic acid and water is taken overhead and a bottoms fraction comprising concentrated cobalt acetate and/or formate is removed from said evaporator;
(e) recycling said cobalt acetate and/or cobalt formate to supply said cobalt acetate and/or formate in step (a); and
(f) recovering an aldehyde.

* * * * *